(12) United States Patent
Maiman

(10) Patent No.: US 11,576,630 B1
(45) Date of Patent: Feb. 14, 2023

(54) RADIATION SHIELDING EYE MASK

(71) Applicant: Maico Mgmt., LLC, Pacific Palisades, CA (US)

(72) Inventor: Stephen Benjamin Maiman, Pacific Palisades, CA (US)

( * ) Notice: Subject to any disclaimer, the term of this patent is extended or adjusted under 35 U.S.C. 154(b) by 0 days.

(21) Appl. No.: 17/940,701

(22) Filed: Sep. 8, 2022

(51) Int. Cl.
*A61B 6/10* (2006.01)
*G21F 1/12* (2006.01)
*A61B 6/14* (2006.01)

(52) U.S. Cl.
CPC .............. *A61B 6/107* (2013.01); *A61B 6/14* (2013.01); *G21F 1/125* (2013.01)

(58) Field of Classification Search
CPC ............ A61B 6/107; A61B 6/14; G21F 1/125
USPC ......... 250/505.1, 506.1, 507.1, 515.1, 516.1, 250/517.1, 518.1, 519.1
See application file for complete search history.

(56) References Cited

U.S. PATENT DOCUMENTS

| | | | |
|---|---|---|---|
| 4,021,862 | A | 5/1977 | Glasser et al. |
| 4,024,405 | A | 5/1977 | Szot |
| 4,938,233 | A | 7/1990 | Orrison, Jr. |
| 8,354,658 | B1 | 1/2013 | Smith et al. |
| 10,617,371 | B2 | 4/2020 | Ballsieper et al. |
| 2004/0041107 | A1* | 3/2004 | Cadwalader ............ G21F 1/106 250/519.1 |
| 2011/0163248 | A1 | 7/2011 | Beck |
| 2020/0306497 | A1* | 10/2020 | Herrador ................. A61L 9/127 |

FOREIGN PATENT DOCUMENTS

CN 214912764 U 11/2021

OTHER PUBLICATIONS

Encyclopedia Britannica (https://www.britannica.com/science/radiation/Damage-to-genes-mutations) "Damage to genes (mutations)"—"Gene mutations resulting from radiation-induced damage to DNA have been produced experimentally in many types of organisms."
Hwang, et al., "Health effects from exposure to dental diagnostic X-ray" (https://www.ncbi.nlm.nih.gov/pmc/articles/PMC6341170/#:~:text=Several%20studies%20have%20found%20an,cancer%20%5B16%2C17%5D.) Introduction section: "Several studies have found an association between dental X-ray exposure and increased risks of brain sancer, tumors of the parotid gland and breast cancer and thyroid cancer."

(Continued)

*Primary Examiner* — Nicole M Ippolito
(74) *Attorney, Agent, or Firm* — Trojan Law Offices

(57) ABSTRACT

An eye mask apparatus for protecting a patient's eyes during dental or other radiography (i.e., "x-rays") has an eye covering portion including a lead vinyl sheet. The lead vinyl sheet has a perimeter configured such that the lead vinyl sheet can completely cover a patient's eyes. The eye covering portion includes a first side and a second side. A trim portion extends around the perimeter, with the trim portion extending inward over a portion of the first side and the second side. A retaining band is coupled to the eye covering portion at a first attachment point and a second attachment point. The retaining band is configured to hold the eye covering portion against the patient's eyes when the mask is worn.

16 Claims, 4 Drawing Sheets

(56) References Cited

OTHER PUBLICATIONS

Chodick, et al., "Risk of Cataract after Exposure to Low Doses of Ionizing Radiation: A 20-Year Prospective Cohort Study among US Radiologic Technologists" (https://www.ncbi.nlm.nih.gov/pmc/articles/PMC2727195/) Sep. 15, 2008, Abstract section: "The lens is relatively radiosensitive, and cataract formation has long been documented as a major ocular complication associated with exposure to ionizing radiation."

Jacob, et al., "Occupational cataracts and lens opacities in interventional cardiology (O'CLOC study): are X-Rays involved?" (https://bmcpublichealth.biomedcentral.com/articles/10.1186/1471-2458-10-537#) Sep. 8, 2010, Abstract section: "Interventional cardiologists are repeatedly and acutely exposed to scattered ionizing radiation (X-rays) during the diagnostic and therapeutic procedures they perform. These "low" exposures may cause damage to the lens of the eye and induce early cataracts, known as radiation-induced cataracts."

Infab, LLC Product Specifications and Technical Data for Low Friction Skinned Vinyl Sheet.

* cited by examiner

RADIATION SHIELDING EYE MASK

FIELD OF THE INVENTION

The present disclosure relates generally to radiation shielding. More specifically, the disclosure relates to a radiation shielding apparatus worn by a user. In particular, the disclosure relates to radiation shielding eye masks for covering a patient's eyes to attenuate electromagnetic radiation flux across a patient's eyes relative to a radiation source, including from dental x-ray imaging. The apparatus of the present disclosure is designed for use in the field of medical radiography including as it relates to dental medicine.

BACKGROUND

In the field of dentistry, x-rays are taken during routine examinations to enable early identification of tooth decay, tooth impaction, periodontal disease, and a host of other conditions which may not yet be visible to the naked eye of a practitioner. Dental x-rays are also frequently taken when patients are experiencing pain, to provide the examining dentist with an accurate picture of what is happening inside a patient's teeth, jaw, and surrounding areas. Dental x-rays are, therefore, an essential diagnostic tool for dental professionals tasked with investigating and maintaining their patients' oral health.

However, studies have shown that exposure to ionizing radiation, such as x-rays, can damage DNA in human cells. This can lead to mutations and, in worst-case scenarios, cancers. In fact, several studies have found an association between dental x-ray exposure and increased risk of brain cancer, tumors of the parotid gland, breast cancer, and thyroid cancer. The sensitive tissues of the eyes are especially susceptible to radiation damage, and studies have shown a correlation between dental x-rays and cataracts. To avoid undue exposure, standard practice is for dentists and dental professionals to use protective gear when performing dental x-ray imaging.

Such protective gear historically has consisted simply of a lead apron draped over a patient's body to shield it from both direct and scattered radiation. Although these traditional aprons work well, they typically weigh upwards of 15 pounds, which can be uncomfortable for those patients unaccustomed to supporting that amount of weight and pressure across their bodies. Lead aprons also fail to protect a patient's head region, and sensitive organs contained therein such as a patient's eyes.

Recent innovations in the field have produced lighter-weight radiation shields made from pliable materials that are more comfortable for the patients who use them. For example, disposable radiological garments may be made from a flexible polymer filled with a non-lead attenuating filler, such as barium sulfate. Also, flexible, lightweight radiation shields may be provided with two layers; one with elements having high atomic numbers, and another with elements having mid-atomic numbers, to absorb high energy direct beam radiation and lower energy backscattered radiation, respectively. This scattered/backscattered radiation is a serious enough issue that other devices have been made with a similar two-layer shield, directed to avoiding and shielding against scattered radiation in particular.

For eye protection during dental radiography, goggles or glasses have been the traditional means for radiation attenuation. Goggles or glasses-type shields are known comprising a lead-impregnated lens, surrounded by a lead vinyl casing to prevent radiation from entering the patient's eyes from the periorbital areas. Other goggles-type shields teach shields that can accommodate more than one type of radiation protection, i.e., β-radiation and/or x-ray radiation and/or gamma radiation. However, these goggles and glasses-type shields often protrude from the patient's face and hinder the administration of the dental x-rays. That is, they get in the way of the x-ray equipment or interfere with the x-rays so that proper images cannot be rendered.

Some known devices seek to remedy this problem by teaching eye shades made from pliable rubber, containing a lead plaster coating for radiation attenuation. The eye shades lie directly against a patient's face. This effectively eliminates the protrusion problem that the goggles and glasses-type shields cause. Yet, because the structure is such that there are two eye shades, with space between the eye shades as well as around the orbital area in general, there is again the risk of scattered radiation entering the patient's eyes and causing damage. Therefore, there is a need for an eye mask that confers sufficient ocular protection from dental x-rays, and does so in a manner that does not hinder or obstruct the dental x-ray imaging process.

SUMMARY

An eye mask apparatus for protecting a patient's eyes during dental radiography is disclosed. The apparatus includes an eye covering portion including a lead vinyl sheet. The eye covering portion has a perimeter, such that the lead vinyl sheet is preferably configured to completely cover the patient's eyes. The eye covering portion also has a first side facing away from the patient's face, and a second side resting against the patient's face. A trim portion extends around the perimeter. The trim portion preferably extends over the perimeter and inward over at least a small portion of the first side and the second side.

A retaining band is coupled to the lead vinyl sheet. In one implementation, the retaining band is coupled to both the lead vinyl sheet and the trim portion. The retaining band, may be attached to both the lead vinyl sheet and the trim portion, each one at a first attachment point and at a second attachment point. The first attachment point and the second attachment point may also be on opposing ends of the perimeter of the lead vinyl sheet. Additionally, the first attachment point and the second attachment point may be on the second side of the lead vinyl sheet. Thus, the retaining band is configured to hold the eye covering portion against the patient's eyes.

The lead vinyl sheet may include or be made from a single unbroken sheet of material. In one implementation, the trim portion may be made of a fabric material. A stitching may also be provided. The stitching may be configured to affix the trim portion to the lead vinyl sheet. The stitching can be configured to affix the trim portion and the retaining band to the lead vinyl sheet at the first attachment point and the second attachment point.

In various alternative implementations, the lead vinyl sheet may be constructed to provide increased or decreased levels of protection against radiation. In one implementation, the lead vinyl sheet may have a thickness of 0.87 mm, a lead equivalent value of 0.125 mm, and a weight of 2.18 kg/m$^2$. In another implementation, the lead vinyl sheet may have a thickness of 1.02 mm, a lead equivalent value of 0.175 mm, and a weight of 2.86 kg/m$^2$. In yet another implementation, the lead vinyl sheet has a thickness of 1.26 mm, a lead equivalent value is 0.250 mm, and a weight of 3.88 kg/m$^2$. In another implementation, the lead vinyl sheet may have a thickness of 1.57 mm, a lead equivalent value of 0.350 mm, and a weight of 5.24 kg/m².

In another implementation, the lead vinyl sheet may have a thickness of 1.73 mm, a lead equivalent value of 0.400 mm, and a weight of 5.92 kg/m². In another implementation, the lead vinyl sheet may have a thickness of 2.05 mm, a lead equivalent value of 0.500 mm, and a weight of 7.28 kg/m². In yet another implementation, the lead vinyl sheet may have a thickness of 3.62 mm, a lead equivalent value of 1.000 mm, and a weight of 14.08 kg/m².

In order to form a mask apparatus for protecting a patient's eyes during dental radiography, a lead vinyl sheet is first provided. The lead vinyl sheet is formed into a shape configured to cover the patient's eyes when worn by the patient. A trim portion is provided and placed around the lead vinyl sheet. Before placement of the trim portion, or alternatively after placement of the trim portion, a retaining band is provided. The retaining band is affixed to the trim portion and, preferably, to the lead vinyl sheet. The retaining band is configured to hold the lead vinyl sheet against the patient's eyes.

The trim portion may optionally be sewn to the lead vinyl sheet. Additionally, the retaining band may be provided with elasticity. The retaining band may be affixed to a first attachment point and a second attachment point, which may be at opposite ends of a perimeter of the lead vinyl sheet. In one alternative implementation, the retaining band may be sewn to a first attachment point and to a second attachment point to affix it to the lead vinyl sheet.

DESCRIPTION

Figure 1:
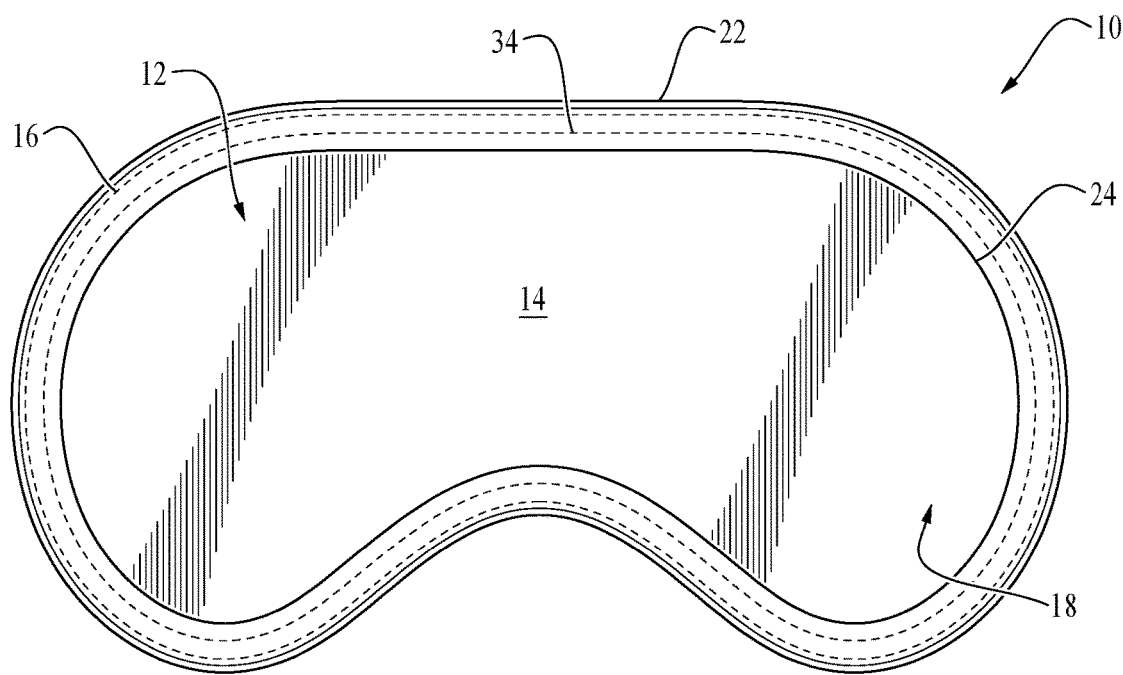
FIG. 1 illustrates a front elevation view of a radiation shielding eye mask.

Referring to FIG. 1, an eye mask apparatus 10 for protecting a patient's eyes during dental or other radiography (i.e., "x-rays") has an eye covering portion 12 including a lead vinyl sheet 14. The lead vinyl sheet 14 has a perimeter 16, and the perimeter 16 is configured such that the lead vinyl sheet 14 completely covers a patient's eyes (not shown). The coverage may, for example, be described as similar to, but is in no way limited by the coverage a typical sleep mask provides. Preferably, the coverage includes not only the patient's eyes, but the areas of the patient's face surrounding the patient's eyes. Alternatively, the coverage may be greater, covering a larger portion of the patient's face, including the patient's eyes.

Figure 2:
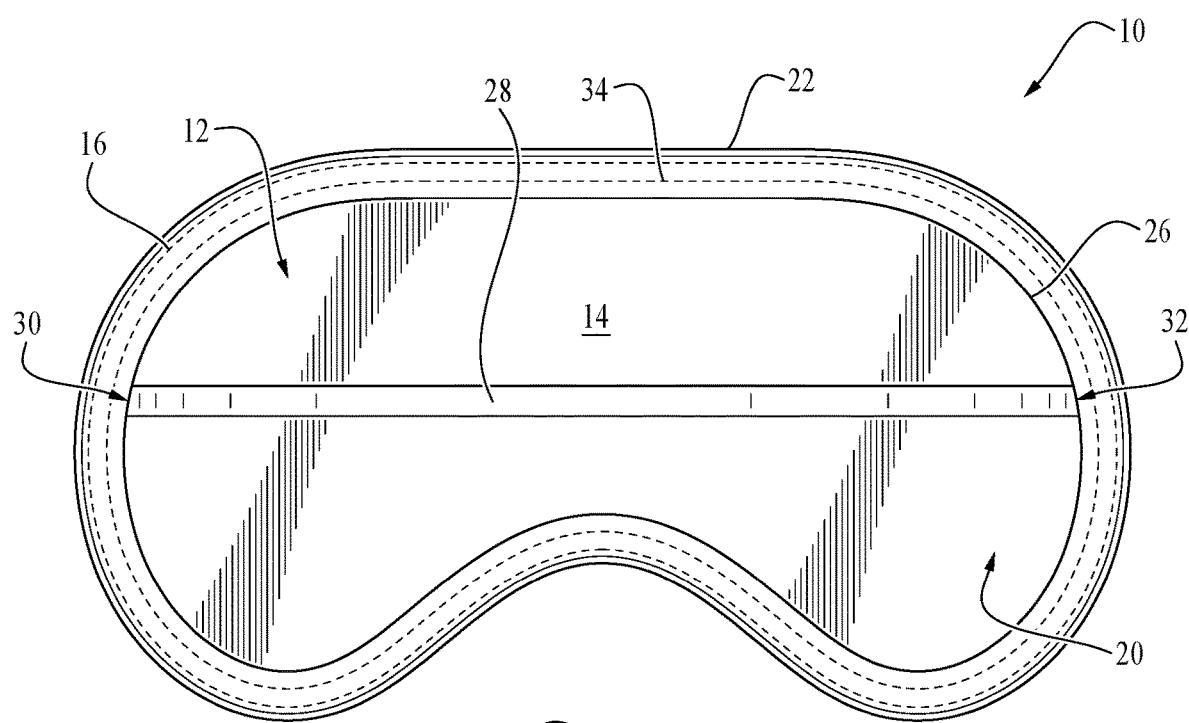
FIG. 2 illustrates a rear elevation view of the radiation shielding eye mask.

The eye covering portion 12, and thus the lead vinyl sheet 14 preferably includes a first side 18 and a second side 20 (FIG. 2). A trim portion 22 extends around the perimeter 16 of the lead vinyl sheet 14. The trim portion 22 is configured to wrap around the perimeter 16 of the lead vinyl sheet 14 both to protect perimeter 16, and to present a more aesthetically pleasing configuration of the eye covering portion 12.

Preferably, the trim portion 22 wraps around the perimeter 16 and extends inward slightly over the first side 18 and the second side 20 to a first trim edge 24 on the first side 18 of the lead vinyl sheet 14, and a second trim edge 26 (FIG. 2) on the second side 20 of the lead vinyl sheet 14.

Referring to FIG. 2, a retaining band 28 is provided and coupled to the eye covering portion 12. In one implementation, the retaining band 28 is coupled to the eye covering portion 12 at a first attachment point 30 and a second attachment point 32. The retaining band 28 may be coupled to both the lead vinyl sheet 14 and the trim portion 22 of the eye covering portion 12 for a more secure anchorage. The retaining band 28 is preferably of a size and tensile strength, such that it holds the eye covering portion 12 against the patient's eyes when the eye mask apparatus 10 is worn by the patient.

Preferably, the lead vinyl sheet 14 may be made from a single unbroken sheet of a lead vinyl material. In some implementations, the trim portion 22 may be a fabric material to provide a softer covering around the perimeter 16 and a more aesthetic appearance to the eye mask apparatus 10. Whether the trim portion 22 is fabric or another material, it may be affixed to the lead vinyl sheet with stitching 34. The stitching 34 may extend entirely around the perimeter 16. Optionally, the stitching 34 may be configured to affix the trim portion 22 and the retaining band 28 to the lead vinyl sheet 14 at the first attachment point 30 and the second attachment point 32.

Figure 3:
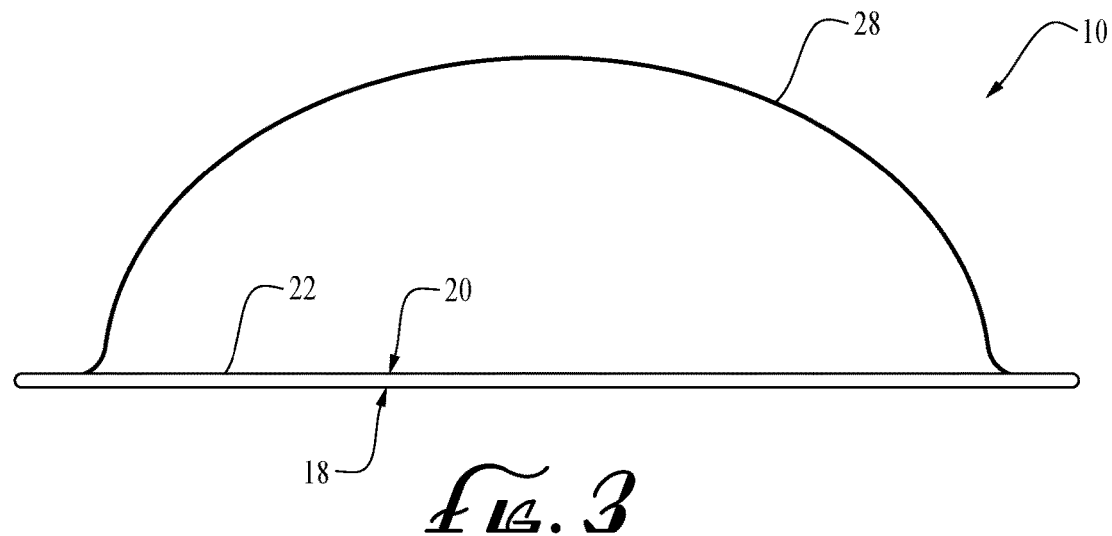
FIG. 3 illustrates a top view of the radiation shielding eye mask.
Figure 4:
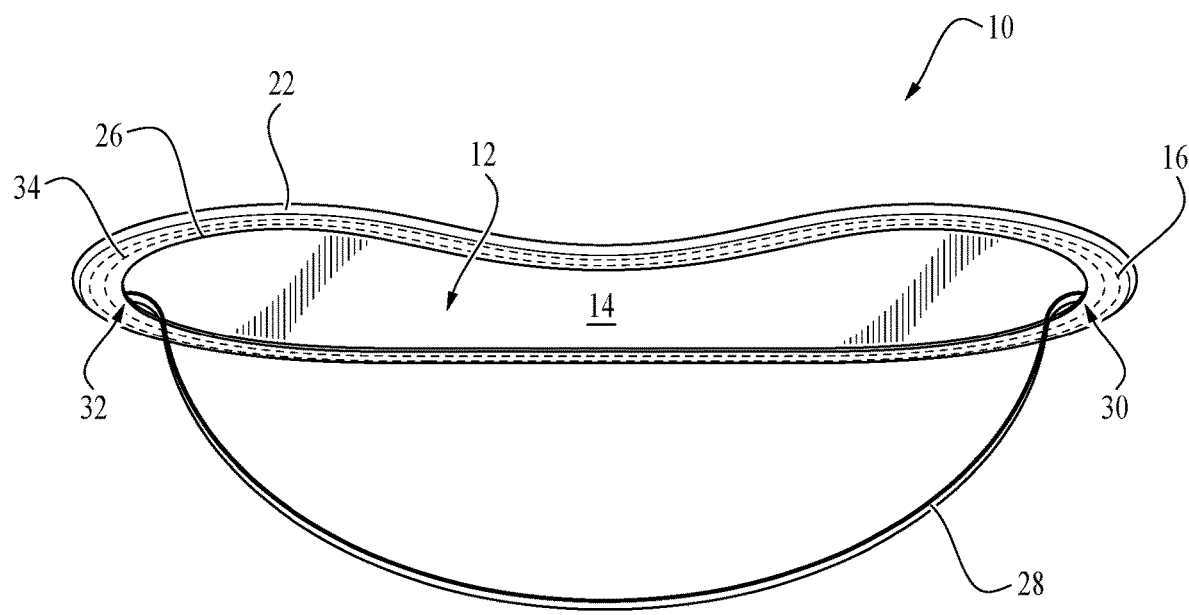
FIG. 4 illustrates a bottom perspective view of the radiation shielding eye mask.
Figure 5:
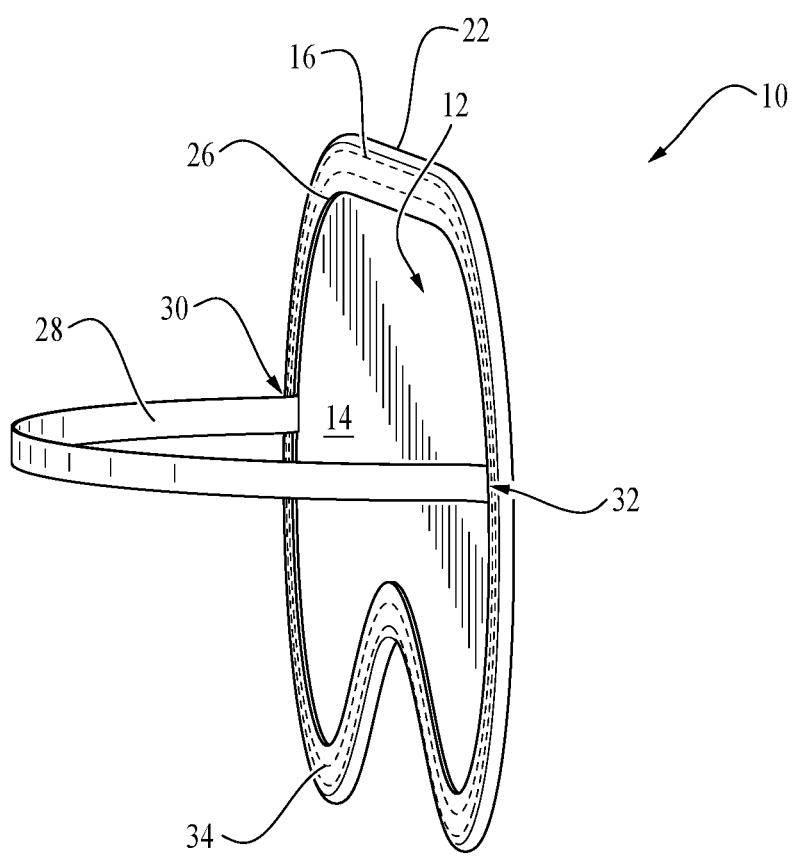
FIG. 5 illustrates a right perspective view of the radiation shielding eye mask.

FIGS. 3, 4, and 5 show a top view, a bottom perspective view, and a right side perspective view, respectively, of the eye mask apparatus 10. FIGS. 3 and 5 in particular illustrate how the trim portion 22 extends around the perimeter 16, and is sewn onto the lead vinyl sheet 14. As illustrated, the retaining band 28 is sewn under the trim portion 22 between the lead vinyl sheet 14 and the trim portion 22 to securely anchor it to the eye covering portion 12. In one implementation, the retaining band 28 may extend all the way to the perimeter 16 of the lead vinyl sheet 14.

Figure 6:
FIG. 6 illustrates a perspective view of the eye mask being worn by a patient positioned to undergo x-ray radiation.

FIG. 6 illustrates a user 100 wearing the eye mask apparatus 10 on the user's head 102 in preparation for a dental x-ray or other radiation treatment.

The lead vinyl sheet 14 is preferably characterized by a thickness between the first side 18 and the second side 20. For radiation protection, the lead vinyl sheet 14 is also preferably characterized by a lead equivalent value. The thickness and lead equivalent value contribute to the weight value of the lead vinyl sheet 14. In one implementation the lead vinyl sheet 14 has a thickness of 0.87 mm, a lead equivalent value of 0.125 mm, and a weight of 2.18 kg/m². Alternative implementations of heavier lead vinyl sheets 14 are described as follows:

One alternative lead vinyl sheet 14 has a thickness of 1.02 mm, a lead equivalent value of 0.175 mm, and a weight of 2.86 kg/m². Another alternative lead vinyl sheet 14 has a thickness of 1.26 mm, a lead equivalent value of 0.250 mm, and a weight of 3.88 kg/m². Another alternative lead vinyl sheet 14 has a thickness of 1.57 mm, a lead equivalent value of 0.350 mm, and a weight of 5.24 kg/m². Another alternative lead vinyl sheet 14 has a thickness of 1.73 mm, a lead equivalent value of 0.400 mm, and a weight of 5.92 kg/m². Another alternative lead vinyl sheet 14 has a thickness of 2.05 mm, a lead equivalent value of 0.500 mm, and a weight of 7.28 kg/m². Another alternative lead vinyl sheet 14 has a thickness of 3.62 mm, a lead equivalent value of 1.000 mm, and a weight of 14.08 kg/m².

Exemplary embodiments of this disclosure are described herein, including the best mode known to the inventors for carrying out the disclosure. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. An eye mask apparatus for protecting a patient's eyes during dental radiography, the apparatus comprising:
   an eye covering portion comprising a lead vinyl sheet having a perimeter, the lead vinyl sheet configured to completely cover the patient's eyes;
   the eye covering portion having a first side and a second side;
   a trim portion extending around the perimeter, the trim portion extending inward over a portion of the first side and the second side;
   a retaining band coupled to the eye covering portion at a first attachment point and a second attachment point; and
   wherein the retaining band is configured to hold the eye covering portion against the patient's eyes; and
   wherein the lead vinyl sheet has a thickness of at least 0.87 mm, a lead equivalent value of at least 0.125 mm, and a weight of at least 2.18 kg/m$^2$.

2. The apparatus of claim 1 wherein the lead vinyl sheet comprises a single unbroken sheet of material.

3. The apparatus of claim 1 wherein the trim portion is a fabric material.

4. The apparatus of claim 1 further comprising a stitching configured to affix the trim portion to the lead vinyl sheet.

5. The apparatus of claim 1 further comprising a stitching configured to affix the trim portion and the retaining band to the lead vinyl sheet at the first attachment point and the second attachment point.

6. The apparatus of claim 1 wherein the lead vinyl sheet has a thickness of 1.02 mm, a lead equivalent value of 0.175 mm, and a weight of 2.86 kg/m$^2$.

7. The apparatus of claim 1 wherein the lead vinyl sheet has a thickness of 1.26 mm, a lead equivalent value of 0.250 mm, and a weight of 3.88 kg/m$^2$.

8. The apparatus of claim 1 wherein the lead vinyl sheet has a thickness of 1.57 mm, a lead equivalent value of 0.350 mm, and a weight of 5.24 kg/m$^2$.

9. The apparatus of claim 1 wherein the lead vinyl sheet has a thickness of 1.73 mm, a lead equivalent value of 0.400 mm, and a weight of 5.92 kg/m$^2$.

10. The apparatus of claim 1 wherein the lead vinyl sheet has a thickness of 2.05 mm, a lead equivalent value of 0.500 mm, and a weight of 7.28 kg/m$^2$.

11. The apparatus of claim 1 wherein the lead vinyl sheet has a thickness of 3.62 mm, a lead equivalent value of 1.000 mm, and a weight of 14.08 kg/m$^2$.

12. A method of protecting a patient's eyes during dental radiography, the method comprising:
    providing a lead vinyl sheet having a thickness of at least 0.87 mm, a lead equivalent value of at least 0.125 mm, and a weight of at least 2.18 kg/m$^2$;
    forming the lead vinyl sheet into a shape configured to cover the patient's eyes when worn by the patient;
    providing a trim portion around the lead vinyl sheet;
    providing a retaining band;
    affixing the retaining band to the trim portion and the lead vinyl sheet; and
    configuring the retaining band to hold the lead vinyl sheet against the patient's eyes.

13. The method of claim 12 further comprising the step of sewing the trim portion to the lead vinyl sheet.

14. The method of claim 12 further comprising the step of providing elasticity to the retaining band.

15. The method of claim 13 further comprising the step of affixing the retaining band to a first attachment point and a second attachment point.

16. The method of claim 13 further comprising the step of sewing the retaining band and the trim portion to a first attachment point and a second attachment point.

* * * * *